United States Patent [19]

Iwahashi

[11] Patent Number: 4,938,957

[45] Date of Patent: Jul. 3, 1990

[54] DEODORANT COMPOSITION AND USE THEREOF

[75] Inventor: Takashi Iwahashi, Sagamihara, Japan

[73] Assignee: Aikoh Co., Ltd., Tokyo, Japan

[21] Appl. No.: 187,244

[22] Filed: Apr. 28, 1988

[51] Int. Cl.$^5$ .................................................. A61F 2/60
[52] U.S. Cl. .................................... 424/76.21; 424/47;
424/76.1; 424/76.2; 424/76.4; 424/76.5;
424/76.8
[58] Field of Search .................. 424/47, 76.1–76.9;
528/405, 424; 426/76.1–76.9

[56] References Cited

U.S. PATENT DOCUMENTS 4,275,054 6/1981 Sebag et al. ........................ 424/65

FOREIGN PATENT DOCUMENTS 2102292 2/1983 United Kingdom ................. 424/65

OTHER PUBLICATIONS

"Deodorant Supply to Hawaii Planned", Japan Chemical Week, p. 12, Dec. 11, 1986.

Primary Examiner—Thurman K. Page
Assistant Examiner—P. Prater
Attorney, Agent, or Firm—Larson and Taylor

[57] ABSTRACT

A new deodorant composition is now provided, which comprises as an active ingredient for deodorization a reaction product which is obtained for reacting either polyethyleneimine or ethyleneimine-alkylene oxide copolymer having a molecular weight in the range of from 100 to 5,000 with monochloroacetic acid in a weight ratio of 1:0.3 to 1.0, optionally in association with conventional additives used for deodorizing utility. The deodorant composition according to this invention may efficiently be used to deodorize all bad odors evolved from a wide variety of sources.

6 Claims, No Drawings

DEODORANT COMPOSITION AND USE THEREOF

SUMMARY OF THE INVENTION

This application is a continuation-in part of application Ser. No. 007,455 filed on Jan. 28, 1987, now abandoned.

This invention relates to a new deodorant composition comprising as an active ingredient a reaction product of polyethyleneimine or ethyleneimine-alkylene oxide copolymer with monochloroacetic acid in a specific ratio and optionally appropriate additives, and which is very effective for deodorizing all bad odors emitted from a wide variety of sources including industrial and domestic applications.

BACKGROUND OF THE INVENTION

It is known that the sources of bad and unpleasant odors include ammonia, trimethylamine, aldehydes, hydrogen sulfide, methyl mercaptan, dimethyl sulfide, fatty acid oxide and mixed gas, with generating alkaline, neutral or acidic smell. As one of the conventional processes of deodorizing bad odors, there may be mentioned a masking method by fragrant materials. According to the nature of bad odors, however, this method has a drawback that bad odors may sometimes be promoted by the fragrant materials employed. As an alternative to the masking method, there may be mentioned a neutralization-deodorization method in which alkaline smell- and acidic smell-generating substances are neutralized by acidic and alkaline materials, respectively, to make them odorless, but this method also has disadvantages that a two-stage operation is required in most cases admitting that it is effective for deodorization of acidic and alkaline odors, respectively, that this method is not applicable to neutral smell and that a further stage of treating neutral smell has to be used in addition to said two-stage operation and hence it causes a complicated multi-stage operation. Further, there may be mentioned a chelating reaction method with use of a sulfonate salt, an adsorption method by porous substances such as active carbon, an oxidative-decomposition method in the presence or absence of a catalyst, a combustion-decomposition method in which a bad smell-generating substance is decomposed to make it odorless and the like, on the basis of which numerous and manifold deodorizers are commercially available for the purpose of deodorization of bad smelling gas. Those conventional deodorization methods are, however, selectively effective only for bad odors generated from the restricted sources, and hence suffer from disadvantages that any combination of the deodorizers and deodorization devices has to be adjusted dependent upon the nature of the bad smelling gas and upon the bad smell-generating sources, that numerous deodorants and deodorization apparatus are often required to deodorize completely all kinds of bad smelling gas and that those methods are complicated and expensive ones. It has been, therefore, sought that a novel deodorizer is developed which is effective to deodorize in one-stage operation all kinds of bad smelling gas including acidic, neutral and alkaline smells generated from a wide variety of sources and which may be employed for wide ranged fields from industrial to domestic uses.

We, the present inventors, have made extensive researches in an attempt to seek for such deodorant composition as dissolving above problems, and we have now found that there may be obtained a novel deodorant composition which comprises as an active ingredient for deodorization a reaction product (present in an amount of 50% by weight or above based on the non-solvent components) obtained by reacting either polyethyleneimine or ethyleneimine-alkylene oxide copolymer having a molecular weight in the range of from 100 to 5000 with monochloroacetic acid in a weight ratio of 1:0.3 to 1.0 and that this deodorant composition may be highly effective to deodorize all kinds of bad and unpleasant odor gas including acidic, neutral and alkaline smells evolved from various sources in one-stage operation.

DETAILED DESCRIPTION OF THE INVENTION

According to an aspect of this invention, therefore, there is provided a deodorant composition which comprises as an active ingredient for deodorization a reaction product obtained by reacting either polyethyleneimine or ethyleneimine-alkylene oxide copolymer of a molecular weight of from 100 to 5000 with monochloroacetic acid in a weight ratio of 1:0.3 to 1.0, optionally in association with conventional adjuvants used for deodorizing utility.

Now, it is well known that the starting monomer or comonomer, ethyleneimine, for the production of polyethyleneimine or ethyleneimine-alkylene oxide copolymer is strongly basic in its nature, may readily be polymerized in the presence of hydrogen ions into a polymer or copolymer thereof, and that addition of a strong base such as caustic soda to ethyleneimine prevents the latter from polymerizing together and the resultant polymer may be subjected to the similar treatment to prevent it from further polymerization to maintain it within a predetermined value of molecular weight. There are disclosed in a lot of publications that polyethyleneimine results from polymerization of ethyleneimine as represented by the formula:

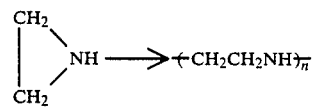

and that the ethyleneimine copolymer is obtained from copolymerization of polyethyleneimine with polyethylene oxide or polypropylene oxide and represented by the formula:

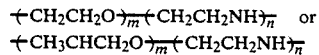

wherein $m \leq n$. As a result of advance of a method for the determination of polymer/copolymer structure, it has been also noticed that a portion of the secondary amine groups ($=NH$) present in the polymer/copolymer is converted into primary amine groups ($-NH_2$) and tertiary amine groups ($\equiv N$) due to high hydrogen activity in the group $=NH$, and that in particular in case of the ethyleneimine copolymer, hydroxyl groups (OH) are formed on the alkylene oxide moiety with resultant of introduction of hydrogen atoms into the alkylene oxide and hence an appreciable portion of the $=NH$ groups is converted into the $\equiv N$ groups, as illustrated by the reaction formula:

$$=NH+-RO = \equiv N+-ROH$$

wherein R represents an alkylene group, i.e. ethylene or propylene group. Polyethylene oxide or polypropylene oxide to be added to polyethyleneimine should be present in an equimolar or less amount.

We have now found that the reaction product of said polymer or copolymer with monochloroacetic acid in a weight ratio of 1:0.3 to 1.0 is highly effective for deodorizing all kinds of bad odors and hence may be used as a deodorizer. When monochloroacetic acid is reacted with the ethyleneimine polymer or copolymer, thus, the primary amine group present in the ethyleneimine moiety is converted through secondary amine group and tertiary amine group into a betaine-typed compound as illustrated by the following equation:

$$-NH_2 + ClCH_2COOH = -NHCH_2COOH + HCl$$

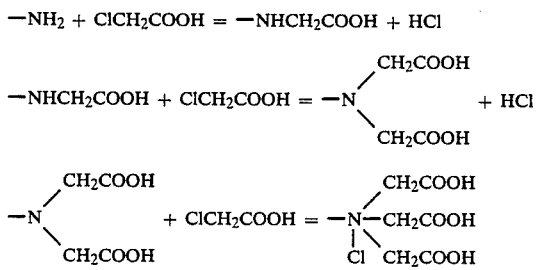

the secondary amine group present in the ethyleneimine moiety is coverted via tertiary amine group into a betaine-typed compound as represented by the equation:

$$=NH + ClCH_2COOH = =N-CH_2COOH + HCl$$

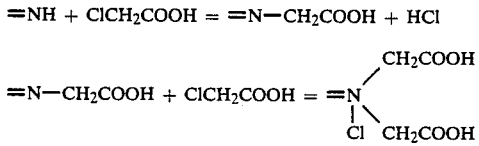

and the tertiary amine group present in the ethyleneimine moiety is converted into a betaine-typed compound as follows:

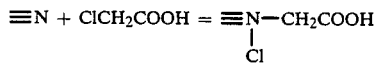

Amongst the above-mentioned reaction processes, the reaction of the primary amine group having a high active hydrogen content with monochloroacetic acid is preferentially started preceeding to the other reactions and hence the conversion of a portion of the primary amine groups into secondary amine group can take place at the minimum even if the reactant, monochloroacetic acid is present in a less amount and hence even if the above reaction cannot be sufficiently conducted to the last. The resultant carboxyl groups (COOH) being acidic ones play a role to absorb an alkaline smell in addition to the fact that an acidic smell can be absorbed by ethyleneimine per se in view of its alkalinity. Accordingly, the reaction of ethyleneimine with monochloroacetic acid is given to impart an ability capable of absorbing further an alkaline smell to the ethyleneimine reactant. Such being the case, the same thing is applicable to the conversion of the secondary amine groups into the tertiary amine groups. The reaction product of the tertiary amine groups with monochloroacetic acid, namely, the betaine-typed compound plays a role of absorbing both alkaline and acidic smells at once in view of the fact that the alkaline smell is absorbed by the resultant carboxyl groups and the acidic smell is absorbed by chlorine atoms attached to the quaternary ammonium group. Some of the betaine-typed compounds may be used as ampholytic surface active agent. In practice, the amount of monochloroacetic acid to be reacted with polyethyleneimine or ethyleneimine-alkylene oxide copolymer should be set in a proportion of not less than 30 parts by weight based on 100 parts by weight of said polymer or copolymer in view of the appreciable deodorizing activity against alkaline smell, although only a portion of amine groups may be reacted with monochloroacetic acid as mentioned above. Namely, the lower limit of the ratio of monochloroacetic acid to ethyleneimine polymer (copolymer) is 0.3. The upper limit of the ratio of monochloroacetic acid to ethyleneimine polymer (copolymer) should be set to 1.0, when the polyethyleneimine or ethyleneimine copolymer component is converted finally to a betaine-typed compound. It is most effective for the reaction product to deodorize both the alkaline and acidic smells if the reaction product is from neutral to weakly acidic in its nature, namely, possesses a pH value of not lower than 5.0. At a pH value lower than 5.0, the reaction product is biased towards deodorization of alkaline smell and hence not practical. The pH value of the resultant reaction product varies dependent upon the molecular weight and composition of the polyethyleneimine or ethyleneimine-alkylene oxide copolymer employed, but the ability capable of deodorizing all bad odors is reached at the most balanced conditions when the ratio of monochloroacetic acid to said polymer or copolymer is in the range of from 0.3 to 1.0.

In case when the reaction product is to be applied to the sources containing a high content of acidic odor-generating substances such as hydrogen sulfide, sulfur dioxide or methylmercaptan, it is preferred to select the reaction product of higher pH value, namely containing a lower proportion of monochloroacetic acid component added. In case when the reaction product is to be applied to the sources containing a high content of alkaline odor-generating substances such as ammonia, trimethylamine or ethylamine, to the contrary, it is preferred to select the reaction product of lower pH value, namely containing a higher proportion of monochloroacetic acid component added. Further, it has proved that the deodorization principle of neutral odor-generating substances such as acetaldehyde, methyl sulfide, acetone or hydrocarbons is based on inclusion action occurring within high molecule of the polyethyleneimine or ethyleneimine copolymer moiety in the reaction product. According to the deodorant composition of this invention, it is practical that the molecular weight of the polyethyleneimine or ethyleneimine copolymer should be in the range of from 300 to 5000 since at a lower molecular weight below 300, the inclusion action is too weak to be practical and at a higher molecular weight above 5000, the reaction product is poor in its solubility and unpractical.

However, it has also proved that the deodorant composition containing the polyethyleneimine or ethyleneimine copolymer of a lower molecular weight in the range of from 100 to 300 exclusive is useful for deodorization of ammonia smell and is of practical use.

Now, we have made further researches on deodorant composition useful for such specific purpose as to deodorize exclusively alkaline smell including ammonia, and we have found that there may also be obtained a new deodorant composition which comprises as an active ingredient for deodorization a reaction product, betaine-type compound prepared by reacting an ethyleneimine (1 mol)-ethylene oxide (2 mols) copolymer (molecular weight: about 150) with monochloroacetic acid in a weight ratio of 1:0.3 to 1.0 and that this deodorant composition is very significantly effective not only for deodorization of unpleasant ammonia smell evolved from pet animals' urine but also for decreasement in stickiness of the deodorant to a carpet or floor mat as compared with the deodorant composition comprising as an active agent said betaine-typed compound containing the starting polymer of a higher molecular weight, namely 300 to 5000.

The attempt to seek for the deodorant composition useful for such the specific usage according to this invention was made on the following ground.

In case when pet animals such as cat and dog excreted urine within the house, the evolution of ammonia gas, one ingredient of bad odors, because increased with the lapse of time. In order to remove substantially ammonia gas, therefore, it has been desired to find a deodorant composition which is selectively reactive with ammonia gas to deodorize it and which is less skicky to a carpet or floor mat when used within a room. Now, it has caused a problem that the deodorant composition containing the polyethyleneimine or ethyleneimine copolymer of a molecular weight of from 300 to 5000 became adhered stickily to the carpet or floor mat because of its higher molecular weight.

As a result of our extensive researches on the deodorant composition as desired, it has been found that the deodorant composition containing the ethyleneimine copolymer of a lower molecular weight of from 100 to 300 exclusive is selectively effective for deodorization of ammonia smell and exhibits a significantly decreased stickiness to the carpet when used.

The deodorant, reaction product, according to this invention is in liquid form and almost soluble in water and organic solvents. In use, the deodorant according to this invention may be used as such or formulated into any form of composition. Thus, it may be diluted with a solvent or admixed with a powdery support to prepare a liquid composition such as an aqueous solution or organic solution or a solid composition such as granules, powder or tablets. The deodorant per se and the resultant liquid or solid composition may directly applied to the bad odor-generating sources or injected in the form of aerosol containing a propellant on the sources. Alternatively, a porous carrier such as active carbon or pumice may be impregnated with the deodorant composition to deodorize a bad odor gas by passing it through the impregnated carrier. The deodorant composition according to this invention in the form of an aqueous solution may practically be used at a minimum concentration in the order of 5% active ingredient and the former in the form of an aerosol sometimes used at a concentration of not higher than 1%.

The deodorant composition according to this invention may comprises, in addition to the active ingredient compound, some conventional additives, for example, surface active agents of imparting either detergent action, dispersion action or bactericidal action to the former, organic and/or inorganic acids or alkaline reagents or oxidizing agents which afford complementary deodorizing activities against specific bad odor-generating sources, and colorants such as dye or pigment and perfumes which improve flavour and color of the resultant deodorant composition. The deodorant composition of this invention should contain a major proportion, i.e. 50% or more, of active ingredient compound based on the total weight of the non-solvent components, in addition to water and an organic/inorganic solvent selected from methyl alcohol, ethyl alcohol, propyl alcohol, ethers, acetone, ethyl acetate, benzene, toluene, xylene, hexane, naphtha, trichloroethylene, tetrachloroethylene, Freon (Trade name: available from E. I. Du Pont) and methyl chloride.

This invention is further illustrated with reference to the following Example to which this invention is in no way limited and which compares the deodorant composition of this invention with a control as to their deodorization efficiency.

EXAMPLE

The deodorant compositions of different monochloroacetic acid/ethyleneimine polymer (copolymer) ratios according to this invention were tested on their deodorizing activities. The test procedure employed was follows. Three types of an atmospheric air containing each 100 ppm of ammonia (alkaline smell), hydrogen sulfide (acidic smell) and acetaldehyde (neutral smell), respectively, were prepared and charged into separate 2000 ml-closed containers. 10 ml portions of the deodorant compositions according to this invention (10 g of active carbon as a control) as shown in the following Table 1 were each introduced into said containers which were then shaken under cap-sealed condition at ambient temperature for one minute, allowed to stand for one hour and finally determined on the concentration of the bad odor gas present in the atmosphere in the upper space thereof. Deodorization rate (%) was calculated from the difference between the concentrations of the bad odor gas before and after the addition of the deodorant and summarized in Table 2 below. Use was made of the Kitagawa typed detecting tube for determination of the bad odor gas concentrations.

TABLE 1

| Test No. | Molecular weight of the starting polymer | Deodorant (The proportion (%) of monochloroacetic acid is based on the stating polymer) | | | |
|---|---|---|---|---|---|
| 1-a | ca. 250 | Ethyleneimine (4 mols)-ethylene oxide (2 mols) copolymer | + | Monochloroacetic acid 20% admixture | 10% aqueous solution |
| 1-b | " | Ethyleneimine (4 mols)-ethylene oxide (2 mols) copolymer | + | Monochloroacetic acid 30% admixture | " |
| 1-c | " | Ethyleneimine (4 mols)-ethylene oxide (2 mols) copolymer | + | Monochloroacetic acid 50% admixture | " |
| 1-d | " | Ethyleneimine (4 mols)-ethylene oxide (2 mols) copolymer | + | Monochloroacetic acid 75% admixture | " |
| 1-e | " | Ethyleneimine (4 mols)-ethylene | + | Monochloroacetic | " |

TABLE 1-continued

Deodorant (The proportion (%) of monochloroacetic acid is based on the stating polymer)

| Test No. | Molecular weight of the starting polymer | | | |
|---|---|---|---|---|
| 1-f | " | Ethyleneimine (4 mols)-ethylene oxide (2 mols) copolymer | + Monochloroacetic acid 100% admixture acid 130% admixture | " |
| 2-a | ca. 300 | Polyethyleneimine | + Monochloroacetic acid 20% admixture | " |
| 2-b | " | Polyethyleneimine | + Monochloroacetic acid 30% admixture | " |
| 2-c | " | Polyethyleneimine | + Monochloroacetic acid 50% admixture | " |
| 2-d | " | Polyethyleneimine | + Monochloroacetic acid 75% admixture | " |
| 2-e | " | Polyethyleneimine | + Monochloroacetic acid 100% admixture | " |
| 2-f | " | Polyethyleneimine | + Monochloroacetic acid 130% admixture | " |
| 3-a | ca. 350 | Ethyleneimine (7 mols)-ethylene oxide (1 mol) copolymer | + Monochloroacetic acid 20% admixture | " |
| 3-b | " | Ethyleneimine (7 mols)-ethylene oxide (1 mol) copolymer | + Monochloroacetic acid 30% admixture | " |
| 3-c | " | Ethyleneimine (7 mols)-ethylene oxide (1 mol) copolymer | + Monochloroacetic acid 50% admixture | " |
| 3-d | " | Ethyleneimine (7 mols)-ethylene oxide (1 mol) copolymer | + Monochloroacetic acid 75% admixture | " |
| 3-e | " | Ethyleneimine (7 mols)-ethylene oxide (1 mol) copolymer | + Monochloroacetic acid 100% admixture | " |
| 3-f | " | Ethyleneimine (7 mols)-ethylene oxide (1 mol) copolymer | + Monochloroacetic acid 130% admixture | " |
| 4-a | ca. 600 | Polyethyleneimine | + Monochloroacetic acid 20% admixture | " |
| 4-b | " | Polyethyleneimine | + Monochloroacetic acid 30% admixture | " |
| 4-c | " | Polyethyleneimine | + Monochloroacetic acid 50% admixture | " |
| 4-d | " | Polyethyleneimine | + Monochloroacetic acid 75% admixture | " |
| 4-e | " | Polyethyleneimine | + Monochloroacetic acid 100% admixture | " |
| 4-f | " | Polyethyleneimine | + Monochloroacetic acid 130% admixture | " |
| 5-a | ca. 1000 | Ethyleneimine (14 mols)-propylene oxide (7 mols) copolymer | + Monochloroacetic acid 20% admixture | " |
| 5-b | " | Ethyleneimine (14 mols)-propylene oxide (7 mols) copolymer | + Monochloroacetic acid 30% admixture | " |
| 5-c | " | Ethyleneimine (14 mols)-propylene oxide (7 mols) copolymer | + Monochloroacetic acid 50% admixture | " |
| 5-d | " | Ethyleneimine (14 mols)-propylene oxide (7 mols) copolymer | + Monochloroacetic acid 75% admixture | " |
| 5-e | " | Ethyleneimine (14 mols)-propylene oxide (7 mols) copolymer | + Monochloroacetic acid 100% admixture | " |
| 5-f | " | Ethyleneimine (14 mols)-propylene oxide (7 mols) copolymer | + Monochloroacetic acid 130% admixture | " |
| 6-a | ca. 1800 | Polyethyleneimine | + Monochloroacetic acid 20% admixture | " |
| 6-b | " | Polyethyleneimine | + Monochloroacetic acid 30% admixture | " |
| 6-c | " | Polyethyleneimine | + Monochloroacetic acid 50% admixture | " |
| 6-d | " | Polyethyleneimine | + Monochloroacetic acid 75% admixture | " |
| 6-e | " | Polyethyleneimine | + Monochloroacetic acid 100% admixture | " |
| 6-f | " | Polyethyleneimine | + Monochloroacetic acid 130% admixture | " |
| 7-a | ca. 4700 | Ethyleneimine (46 mols)-propylene oxide (46 mols) copolymer | + Monochloroacetic acid 20% admixture | " |
| 7-b | " | Ethyleneimine (46 mols)-propylene oxide (46 mols) copolymer | + Monochloroacetic acid 30% admixture | " |
| 7-c | " | Ethyleneimine (46 mols)-propylene oxide (46 mols) copolymer | + Monochloroacetic acid 50% admixture | " |
| 7-d | " | Ethyleneimine (46 mols)-propylene oxide (46 mols) copolymer | + Monochloroacetic acid 75% admixture | " |
| 7-e | " | Ethyleneimine (46 mols)-propylene oxide (46 mols) copolymer | + Monochloroacetic acid 100% admixture | " |
| 7-f | " | Ethyleneimine (46 mols)-propylene oxide (46 mols) copolymer | + Monochloroacetic acid 130% admixture | " |
| 8 | — | — | — | Powdery active carbon |
| 9-a | ca. 150 | Ethyleneimine (1 mol)-ethylene | + Monochloroacetic acid | 10% aqueous |

TABLE 1-continued

Deodorant (The proportion (%) of monochloroacetic acid is based on the stating polymer)

| Test No. | Molecular weight of the starting polymer | | |
|---|---|---|---|
| 9-b | " | Ethyleneimine (1 mol)-ethylene oxide (2 mols) copolymer | 30% admixture + Monochloroacetic acid 50% admixture | solution " |
| 9-c | " | Ethyleneimine (1 mol)-ethylene oxide (2 mols) copolymer | + Monochloroacetic acid 65% admixture | " |
| 9-d | " | Ethyleneimine (1 mol)-ethylene oxide (2 mols) copolymer | + Monochloroacetic acid 75% admixture | " |
| 9-e | " | Ethyleneimine (1 mol)-ethylene oxide (2 mols) copolymer | + Monochloroacetic acid 100% admixture | " |

TABLE 2

| Test No. | Components of bad odors | | |
|---|---|---|---|
| | Ammonia | Hydrogen sulfide | Acetaldehyde |
| 1-a | 61.5 | 100.0 | 43.4 |
| 1-b | 70.3 | 100.0 | 50.6 |
| 1-c | 74.5 | 100.0 | 52.5 |
| 1-d | 86.7 | 85.5 | 55.6 |
| 1-e | 100.0 | 63.3 | 63.6 |
| 1-f | 100.0 | 50.6 | 70.5 |
| 2-a | 73.8 | 100.0 | 81.3 |
| 2-b | 90.8 | 100.0 | 90.5 |
| 2-c | 93.6 | 97.5 | 91.6 |
| 2-d | 98.6 | 97.0 | 93.5 |
| 2-e | 100.0 | 93.0 | 95.1 |
| 2-f | 100.0 | 84.7 | 98.3 |
| 3-a | 80.1 | 100.0 | 94.5 |
| 3-b | 91.0 | 100.0 | 95.8 |
| 3-c | 94.5 | 100.0 | 97.8 |
| 3-d | 99.4 | 100.0 | 98.8 |
| 3-e | 100.0 | 95.3 | 97.6 |
| 3-f | 100.0 | 83.4 | 97.0 |
| 4-a | 82.3 | 100.0 | 95.5 |
| 4-b | 93.5 | 100.0 | 95.7 |
| 4-c | 95.1 | 97.7 | 96.8 |
| 4-d | 99.5 | 96.7 | 97.6 |
| 4-e | 100.0 | 91.0 | 100.0 |
| 4-f | 100.0 | 87.3 | 100.0 |
| 5-a | 85.7 | 100.0 | 95.0 |
| 5-b | 92.5 | 100.0 | 97.3 |
| 5-c | 95.6 | 98.0 | 98.0 |
| 5-d | 95.8 | 97.5 | 98.0 |
| 5-e | 100.0 | 95.3 | 98.5 |
| 5-f | 100.0 | 85.7 | 100 |
| 6-a | 85.6 | 100.0 | 100.0 |
| 6-b | 90.8 | 98.7 | 100.0 |
| 6-c | 93.1 | 97.9 | 100.0 |
| 6-d | 97.8 | 98.1 | 100.0 |
| 6-e | 98.8 | 93.5 | 100.0 |
| 6-f | 100.0 | 89.7 | 100.0 |
| 7-a | 88.4 | 100.0 | 95.7 |
| 7-b | 90.5 | 100.0 | 96.2 |
| 7-c | 94.7 | 97.7 | 98.3 |
| 7-d | 97.8 | 97.5 | 97.8 |
| 7-e | 98.5 | 94.4 | 99.5 |
| 7-f | 100.0 | 89.1 | 99.0 |
| 8 | 15.3 | 90.7 | 7.6 |
| 9-a | 85.1 | 55.4 | 0 |
| 9-b | 99.3 | 23.2 | 0 |
| 9-c | 100.0 | 10.1 | 0 |
| 9-d | 100.0 | 0 | 0 |
| 9-e | 100.0 | 0 | 0 |

As obvious from above Table 2, use of an active carbon as a control (Test No. 8) exhibited 90.7% of deodorization rate against hydrogen sulfide gas so that the deodorant compositions according to this invention should be preferably restricted to those compositions which showed respectively 90% or more of deodorization rate against three types of bad odor gas components. Under these circumstances, the deodorant compositions referred to as Test Nos. 1-a and 1-f; Nos. 2-a, 3-a, 4-a, 5-a, 6-a and 7-a; and Nos. 2-f, 3-f, 4-f, 5-f, 6-f and 7-f, go beyond the scope as defined in the present deodorant composition and hence should be designated as comparative Examples. As clear also from above Table 2, use of the lower molecular weight (e.g. 100 and 250) of the starting polymer affords poor deodorization rate of bad odor gas components including a neutral smell gas, but provides a selective deodorization efficiency against ammonia smell, and therefore falls within the scope as defined in the present deodorant composition. Further, addition of 20% or 130% monochloroacetic acid to the starting polymer is biased towards deodorization of specific bad odor gas and hence unsuitable for deodorization of all kinds of odors.

As mentioned above, the deodorant composition according to this invention is highly active on the deodorization of all kinds of bad odors including acidic, neutral and alkaline smells in only one stage operation so that it may effectively be utilized for the wide range of fields of from industrial to domestic uses against a variety of bad odors.

What we claim is:

1. A deodorant composition which comprises as an active ingredient for deodorization a reaction product obtained by reacting either polyethyleneimine or ethylene-imine-alkylene oxide copolymer having a molecular weight in the range of from 100 to 5000 with monochloroacetic acid in a weight ratio of 1:03 to 1.0.

2. A deodorant composition according to claim 1 in which the ethyleneimine-alkylene oxide copolymer is resulted from addition polymerization of polyethyleneimine and either polyethylene oxide or polypropylene oxide in an equimolar or less amount.

3. A deodorant composition according to claim 1 in which the active ingredient is present in an amount of 50% by weight or above based on the non-solvent components comprising the active ingredient and additives for deodorization selected from organic and/or inorganic acids and salts thereof, alkaline reagents, surface active agents, oxidizing agents, fillers, colorants and perfumes.

4. A deodorant composition according to claim 1 in which it comprises, in addition to the non-solvent components, water and an organic/inorganic solvent taking part in dissolution of said components and selected from methyl alcohol, ethyl alcohol, propyl alcohol, ethers, acetone, ethyl acetate, benzene, toluene, xylene, hexane, naphtha, trichloroethylene, tetrachloroethylene, Freon and methyl chloride.

5. A deodorant composition which comprises as an active ingredient for deodorization a reaction product obtained by reacting either polyethyleneimine or ethyleneimine-alkylene oxide copolymer having a molecular weight in the range of from 100 to 300 with monochloroacetic acid in a weight ratio of 1:0.3 to 1.0.

6. A deodorant composition which comprises as an active ingredient for deodorization a reaction product obtained by reacting either polyethyleneimine or ethyleneimine-alkylene oxide copolymer having a molecular weight in the range of from 300 to 5000 with monochloroacetic acid in a weight ratio of 1:0.3 to 1.0.

* * * * *